(12) United States Patent
Biber et al.

(10) Patent No.: US 7,764,065 B2
(45) Date of Patent: Jul. 27, 2010

(54) ARRANGEMENT FOR TRANSMISSION OF MAGNETIC RESONANCE SIGNALS

(75) Inventors: Stephan Biber, Erlangen/Frauenaurach (DE); Helmut Greim, Adelsdorf (DE); Joerg Rothard, Litzendorf (DE); Markus Vester, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 115 days.

(21) Appl. No.: 12/243,056

(22) Filed: Oct. 1, 2008

(65) Prior Publication Data
US 2009/0096456 A1    Apr. 16, 2009

(30) Foreign Application Priority Data
Oct. 1, 2007    (DE) ............... 10 2007 047 020

(51) Int. Cl.
*G01V 3/00* (2006.01)
(52) U.S. Cl. .................. 324/318; 324/322
(58) Field of Classification Search ......... 324/300–322; 600/407–445; 128/653.2, 653.3; 343/742–744, 343/896
See application file for complete search history.

(56) References Cited

U.S. PATENT DOCUMENTS

| | | | |
|---|---|---|---|
| 4,680,549 A | | 7/1987 | Tanttu |
| 4,689,564 A | * | 8/1987 | Leue et al. .................. 324/309 |
| 6,157,193 A | | 12/2000 | Renz et al. |
| 6,552,546 B2 | | 4/2003 | Greim |
| 7,221,162 B2 | * | 5/2007 | Feiweier et al. ............. 324/318 |
| 7,265,546 B2 | * | 9/2007 | Kannengiesser et al. .... 324/309 |
| 7,345,478 B2 | * | 3/2008 | Lieblich et al. ............. 324/300 |
| 7,375,523 B1 | * | 5/2008 | Hancu ........................ 324/307 |
| 7,443,166 B2 | * | 10/2008 | Heid .......................... 324/322 |
| 7,535,230 B2 | * | 5/2009 | Takagi ....................... 324/318 |
| 2006/0197633 A1 | * | 9/2006 | Lee ............................ 333/231 |
| 2007/0210793 A1 | * | 9/2007 | Kiefer ........................ 324/307 |
| 2008/0024129 A1 | * | 1/2008 | Heid .......................... 324/307 |

FOREIGN PATENT DOCUMENTS

WO    WO 2006/090293    8/2006

OTHER PUBLICATIONS

"The NMR Phased Array," Roemer et al., Magnetic Resonance in Medicine, vol. 16 (1990) pp. 192-225.

* cited by examiner

*Primary Examiner*—Brij B Shrivastav
(74) *Attorney, Agent, or Firm*—Schiff Hardin LLP (57) ABSTRACT

An arrangement to transmit magnetic resonance signals has a local coil composed of a number of individual antennas for acquisition of radio-frequency signals of a magnetic resonance examination. Preamplifiers amplify the radio-frequency signals, and a transmission device transmits the radio-frequency signals from the local coil to the preamplifiers. The transmission device is fashioned as a readout coil and has a number of individual antennas. The individual antennas of the readout coil are magnetically coupled with the individual antennas of the local coil, with the individual antennas of the local coil and the individual antennas of the readout coil forming a linear MIMO transmission system describable by a transmission matrix.

20 Claims, 8 Drawing Sheets

---- Standard
—— modified

FIG 8

ARRANGEMENT FOR TRANSMISSION OF MAGNETIC RESONANCE SIGNALS

BACKGROUND OF THE INVENTION

1. Field of the Invention

The invention concerns an arrangement to transfer magnetic resonance signals emitted by individual antennas of a magnetic resonance local coil.

2. Description of the Prior Art

In magnetic resonance apparatuses, magnetic resonance signals are acquired with the use of local coils. A local coil generally is composed of multiple individual antennas that are also designated as "loops". Each loop is generally fashioned as a coil.

During the magnetic resonance examination (data acquisition), excited atomic nuclei induce respective voltages as magnetic resonance signals in the individual antennas of the local coil, which magnetic resonance signals are transferred to a receiver. This transfer generally ensues via wires.

From DE 3500456 A1, U.S. Pat. No. 4,680,549 A1 and DE 19751017 A1 it is known to extend an individual local coil with an oscillating circuit, wherein the local coil is designed as a passive, resonant field concentrator and coupled with a readout coil for signal transmission.

In the acquisition case, a sensitivity gain is advantageously achieved here that corresponds to a concentration of the magnetic field. It is also advantageous that the local coil can be of simple design because, among other things, it requires no power supply.

However, it is disadvantageous that the cited prior art cannot be used without further measures for a local coil that has a number of individual antennas or acquisition coils.

Such a local coil exhibits a number of modes of the magnetic resonance signals (corresponding to the number of individual antennas) that must be transmitted. The modes can be associated with various spatial frequencies. Higher signal modes thereby have field distributions with a shorter range and are strongly attenuated in transmission, with an associated transmission power efficiency decrease and a proportional increase of the noise contribution of the readout coil.

A related problem is that, due to a relatively strong coupling among lower modes, these tend to dominate in the acquisition profile. Primarily due to an imperfect geometry of the local coil (for example a weakly concentric birdcage), it is difficult to read out a short-wave mode without interference due to signal and noise from a low mode.

An additional disadvantage results from the conventional use and associated wiring of low-noise preamplifiers. A low-noise preamplifier that amplifies the signal acquired by the individual antenna is respectively provided for every individual antenna of the readout coil. The individual antennas of the local coil retroact on the readout coil used for signal transmission. The source impedance at which the associated preamplifiers are operated thereby changes. Moreover, inputs of the various preamplifiers are coupled among one another.

An existing, internal preamplifier noise is disadvantageously increased by these two effects.

SUMMARY OF THE INVENTION

An object of the present invention is to provide an improved arrangement for wireless transmission of signals of a local coil of the type described above.

The arrangement according to the invention for transmission of magnetic resonance signals has a local coil formed of a number of individual antennas that acquire radio-frequency signals in a magnetic resonance examination. Preamplifiers are additionally provided with which an amplification of the radio-frequency signals ensues. A transmission device is fashioned to transmit the radio-frequency signals from the local coil to the preamplifiers and connects the individual antennas with the preamplifiers.

The transmission device is fashioned as a readout coil and has a number of individual antennas. The individual antennas of the readout coil are magnetically coupled with the individual antennas of the local coil. Via the coupling, the individual antennas of the local coil and the individual antennas of the readout coil form a linear MIMO transmission system describable by a transmission matrix.

DESCRIPTION OF THE PREFERRED EMBODIMENTS

Figure 1:
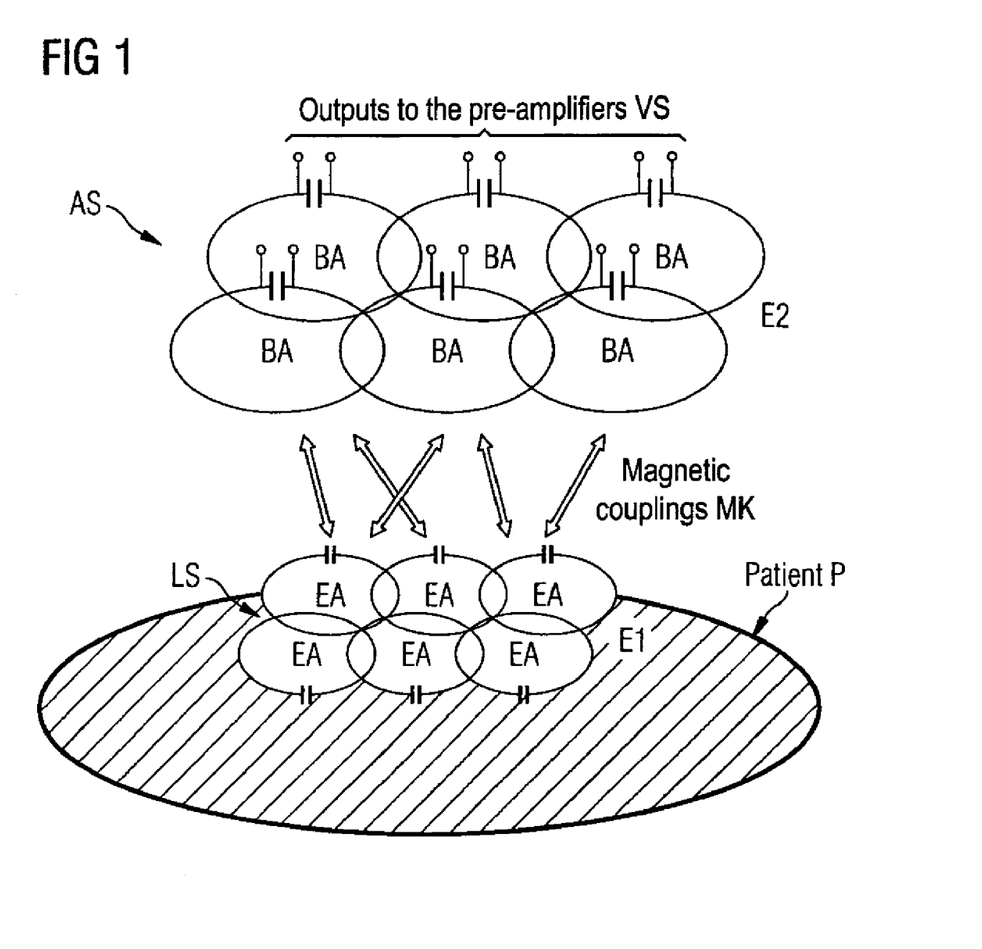
FIG. 1 shows a first embodiment of an inventive arrangement for readout of local coil signals.

FIG. 1 shows a first embodiment of an inventive arrangement.

A local coil LS that has a number of individual receiving antennas EA is provided on a patient P. These are fashioned as coils, for example.

A readout coil AS is additionally provided that has a number of individual antennas BA. The individual antennas BA serve to transmit signals that are acquired via the individual antennas EA of the local coil LS to a number of preamplifiers VS.

For example, a preamplifier VS is respectively downstream of every individual antenna BA of the readout coil AS and is thus connected therewith.

In a preferred embodiment, the individual antennas EA of the local coil LS or the individual antennas BA of the readout coil AS are arranged in planes E1 and E2 parallel to one another. The two planes exhibit an interval d relative to one another.

The individual antennas BA of the readout coil AS are wirelessly connected with the individual antennas EA of the local coil LS through a magnetic or inductive coupling MK.

A linear MIMO transmission system ("Multiple Input Multiple Output, MIMO") is formed by the magnetic coupling between the individual antennas EA and BA arranged in planes.

Every one of a total of N individual antennas EA couples with each of in total M individual antennas BA, such that the linear MIMO transmission system is defined by an N×M transmission matrix.

Adjacent, resonating individual antennas are increasingly more difficult to differentiate with increasing distance between the local coil LS and the readout coil AS.

The magnetic fields between the coupled individual antennas EA and BA of the periodically coupled coil arrays can be considered in orthogonal, spatial Fourier modes.

It has thereby been shown that the magnetic fields exhibit a shorter range for higher (spatially shorter-wave) modes, and therefore exhibit a coupling factor m multiple times smaller than is the case for longer-wave modes.

The field structures are thus spatially low-pass filtered, wherein $$m \sim \exp(-kd),$$

applies, with m as a magnetic coupling factor, k as a spatial frequency in a coil array that is directly proportional to the mode number, and d as an interval between the individual antennas EA, BA of the local coil LS and the readout coil AS.

This correlation, with the final performances Q of the individual antennas fashioned as coils, leads to a transmission efficiency reduction for spatially higher-frequency modes:

$$eta = 1/(1 + 1/(m^2 Q1 Q2))$$

with:
eta as a power efficiency of the transmission,
Q1 as a performance of the individual antennas EA and
Q2 as a performance of the individual antennas BA.

An available SNR gain near a patient surface is thereby reduced, and an increased additional noise results in a parallel magnetic resonance imaging.

Primarily given a large interval d between the two planes E1 and E2, low modes in particular tend to dominate in the brightness and also in the contribution to the total noise in a formed acquisition image.

In a preferred development, the individual antennas EA of the local coil LS are operated at an increased distance d1 from the patient surface to improve the transmission efficiency, for example at a distance d1 of approximately 3 cm while typical distances are presently approximately 1 cm.

On the one hand, the distance between the individual antennas BA of the readout coil AS and the individual antennas EA of the local coil LS is therefore reduced, and the coupling factor m is thereby advantageously increased. Second, the load or influencing of the individual antennas EA of the local coil LS by the patient P is also advantageously reduced so that the performance Q1 is increased.

Overall, a compromise can be set between the increasing lifting efficiency with regard to the readout coil AS and the decreasing efficiency of the local coil LS.

An additional improvement is achieved by increasing the performance Q2 of the readout coil AS or, respectively, its individual antennas BA. For example, it would be possible to operate the individual antennas BA of the readout coil at cryogenic temperatures (for example at a temperature of 80 K). Both the resistance and the noise temperature of the antenna conductors used would therefore be advantageously reduced. Resistance of the patient dominating at low modes likewise appears reduced in higher modes due to the weak coupling, such that a reduction of the internal noise of the readout antenna is completely effective.

With regard to FIG. 1, the local coil LS is advantageously movable and arranged near the patient P while the readout coil AS is a fixed component of the magnetic resonance apparatus.

Figure 2:
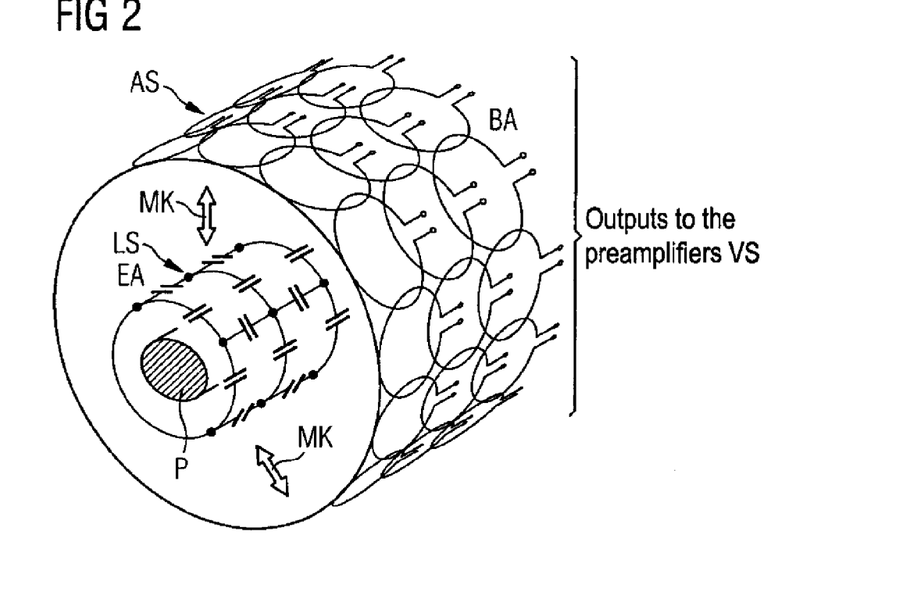
FIG. 2 shows an alternative (relative to FIG. 1) arrangement of individual antennas of the local coil and of the readout coil.

FIG. 2 shows, as an alternative to FIG. 1, an arrangement of the individual antennas EA of the local coil LS and of the individual antennas BA of the readout coil AS.

The individual antennas EA of the local coil LS or, respectively, the individual antennas BA of the readout coil AS are thereby arranged on cylinder walls parallel to one another.

The local coil LS is realized as a birdcage antenna structure, for example. The local coil is preferably designed as a "degenerated birdcage" as described in WO 2006 090293 A1, for example.

Figure 3:
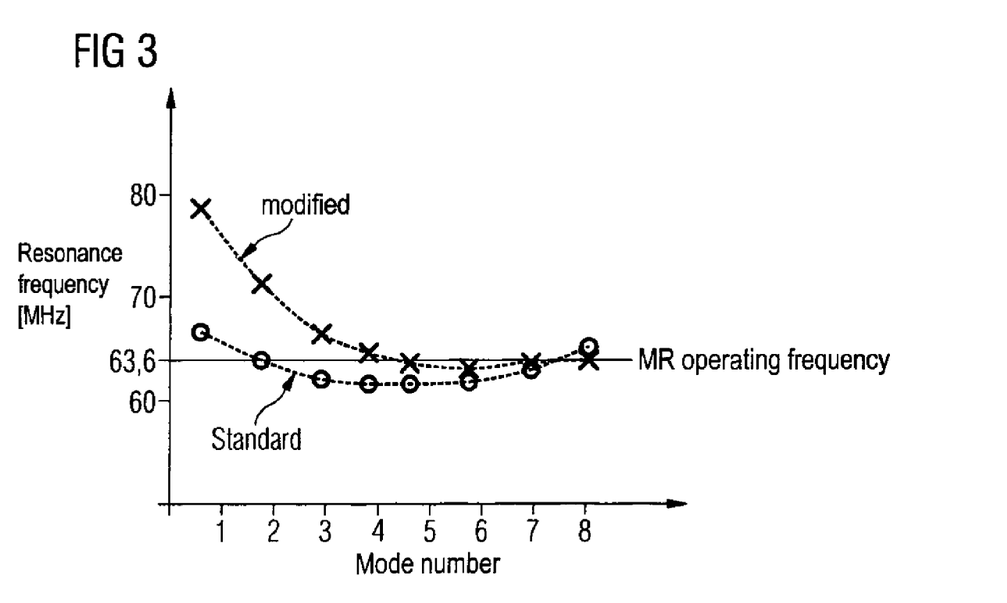
FIG. 3 is a representation of the dispersion of mode resonance frequencies.

FIG. 3 shows a dispersion representation of mode resonance frequencies.

In an advantageous development, targeted couplings between the individual antennas EA of the local coil LS are produced in order to achieve a mode dispersion. The resonance frequency of lower modes is therefore distinctly increased (typically be 20%) so that they lie above the operating frequency of the magnetic resonance apparatus.

The concentration of the fields of the low modes is therefore typically reduced by a factor of 10. Primary and secondary fields are additionally, advantageously superimposed in an equiphase manner.

Figure 4A:
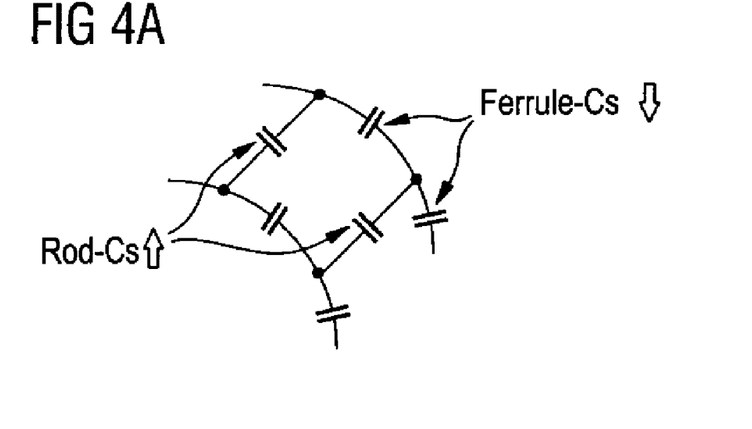
FIGS. 4A, 4B and 4C respectively show three embodiments to adjust the mode dispersion, with regard to FIG. 3.
Figure 4B:
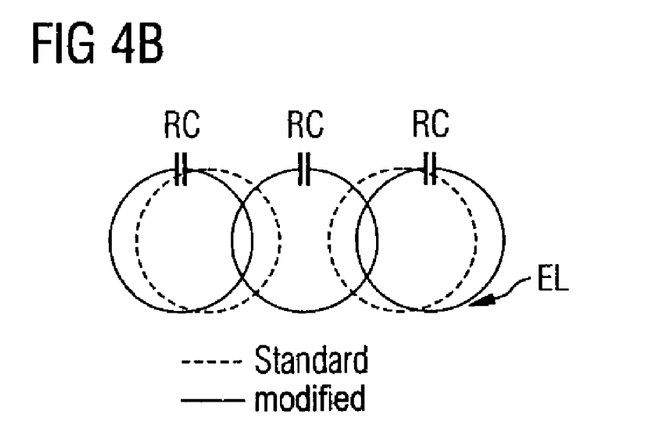
Figure 4C:
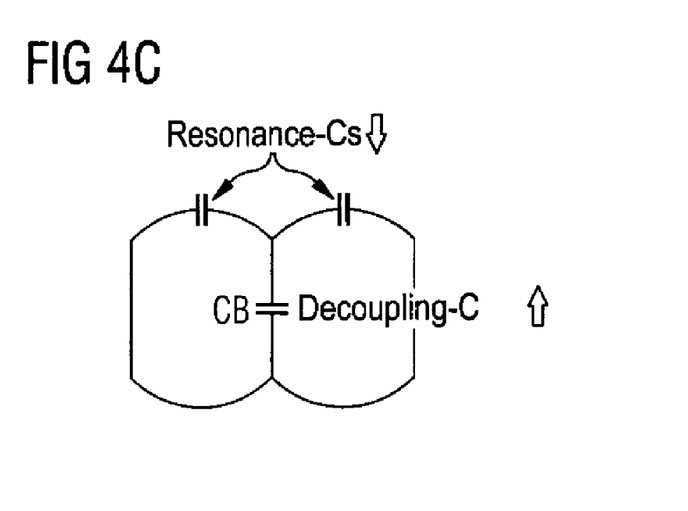

In reference to FIG. 3, FIG. 4 shows in total three embodiments in order to set a suitable mode dispersion.

FIG. 4a shows a known form of a cylindrical acquisition coil or, respectively, local coil that is designed as what is known as a degenerate birdcage. Such a birdcage is described in the printed document WO 2006090293 A, for example.

Normally, rod capacitances (designated as "rod-C") are set so that adjacent birdcage windows are properly decoupled. Only very slight deviation of the resonance frequencies of all utilized modes from the magnetic resonance operating frequency of an MR apparatus results from this.

In the present invention, these rod capacitances "rod-C" are modified such that the desired dispersion materializes. For this the rod capacitances "rod-C" are slightly increased, and at the same time ferrule capacitances (designated as "ferrule-C") are slightly reduced, such that a high-pass birdcage operation is approximated.

The produced modification direction of the capacitance values are indicated in FIG. 4a as arrows directed forwards and backwards.

For example, an adjustment of the degenerate birdcage to a minimal dispersion is produced in a first step to tune the capacitors. The inherent resonances of all modes then lie close to the operating frequency of the MR system.

In a second step, the values of the rod capacitors "rod-C" are increased by approximately 40%, whereby the frequencies of the higher modes are more significantly reduced than those of the low modes.

In a third step, ferrule capacitances ("ferrule-C") are reduced until a fourth mode is resonant at the operating frequency. The basic mode resonance then lies approximately 20% above the operating frequency.

FIG. 4b shows a known "loop array" as an acquisition antenna array or, respectively, as a local coil. A magnetic decoupling of adjacent individual antennas is thereby typically set by a selected overlapping of the adjacent coil loops.

In the present invention, this overlap is now specifically reduced in order to increase the coupling for the mode dispersion.

In a first step, resonance capacitors RC of every individual loop EL are tuned to the operating frequency of the MR apparatus, and in fact in the absence of adjacent loops EL.

The adjustment of the geometric overlap with the goal of a minimal coupling between the adjacent loop EL ensues corresponding to the document "The NMR phased array" by Roemer et al., Magnetic Resonance in Medicine, Volume 16, Issue 2, Pages 192-225.

Overlap surfaces are reduced by approximately 40% in a second step. The resonance frequency of the basic mode therefore rises while that of the higher modes decreases.

In a third step, the resonance capacitors RC are reduced so far that a fourth mode is resonant again at the operating frequency. The basic mode resonance then lies approximately 20% above the operating frequency.

FIG. 4c shows a variant of the loop array described in FIG. 4b in which a decoupling capacitor CB is used in a common conductor instead of the overlap to decouple one loop relative to an adjacent loop.

The tuning of the loops with common capacitor CB ensues as described in FIG. 4a. The capacitor CB in the common conductor corresponds to the rod capacitance "rod-C" while the resonance capacitor "resonance-C" corresponds to the ferrule capacitance.

Figure 5:
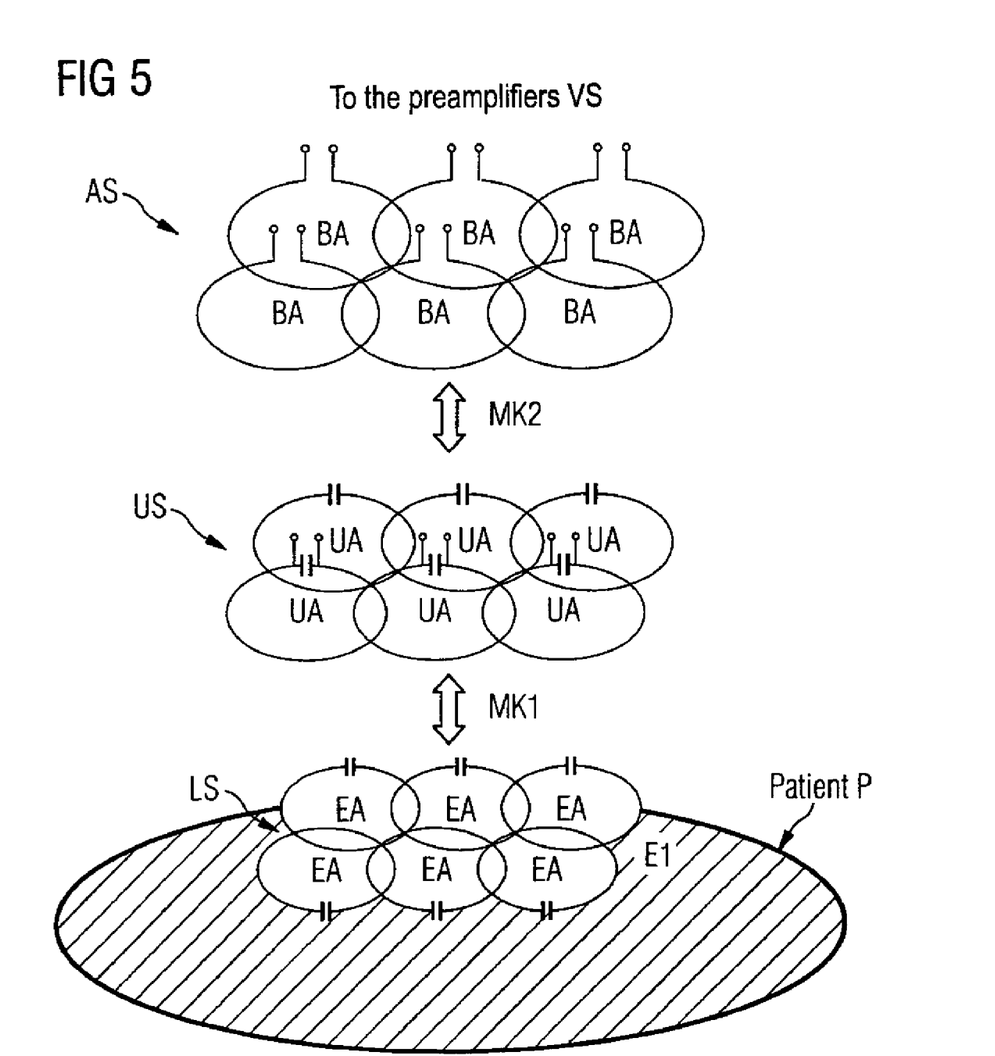
FIG. 5 shows a further embodiment of the arrangement according to the invention.

FIG. 5 shows an advantageous development of the arrangement according to the invention, with an inductive or magnetic coupling designed in two stages.

An additional coil is arranged as a transmission coil US between the local coil LS and the readout coil AS.

The transmission coil US again has a number of individual antennas UA that are designed as coils.

The individual antennas EA of the local coil LS are correspondingly connected with the individual antennas UA of the transmission coil US by a first magnetic coupling MK1 while the individual antennas UA of the transmission coil US are connected with the individual antennas BA of the readout coil AS via a second magnetic coupling MK2.

It is therefore possible to reduce the distances between the respective antenna surfaces so far that an available acquisition signal energy is efficiently handed off, even for shortwave modes.

Figure 6:
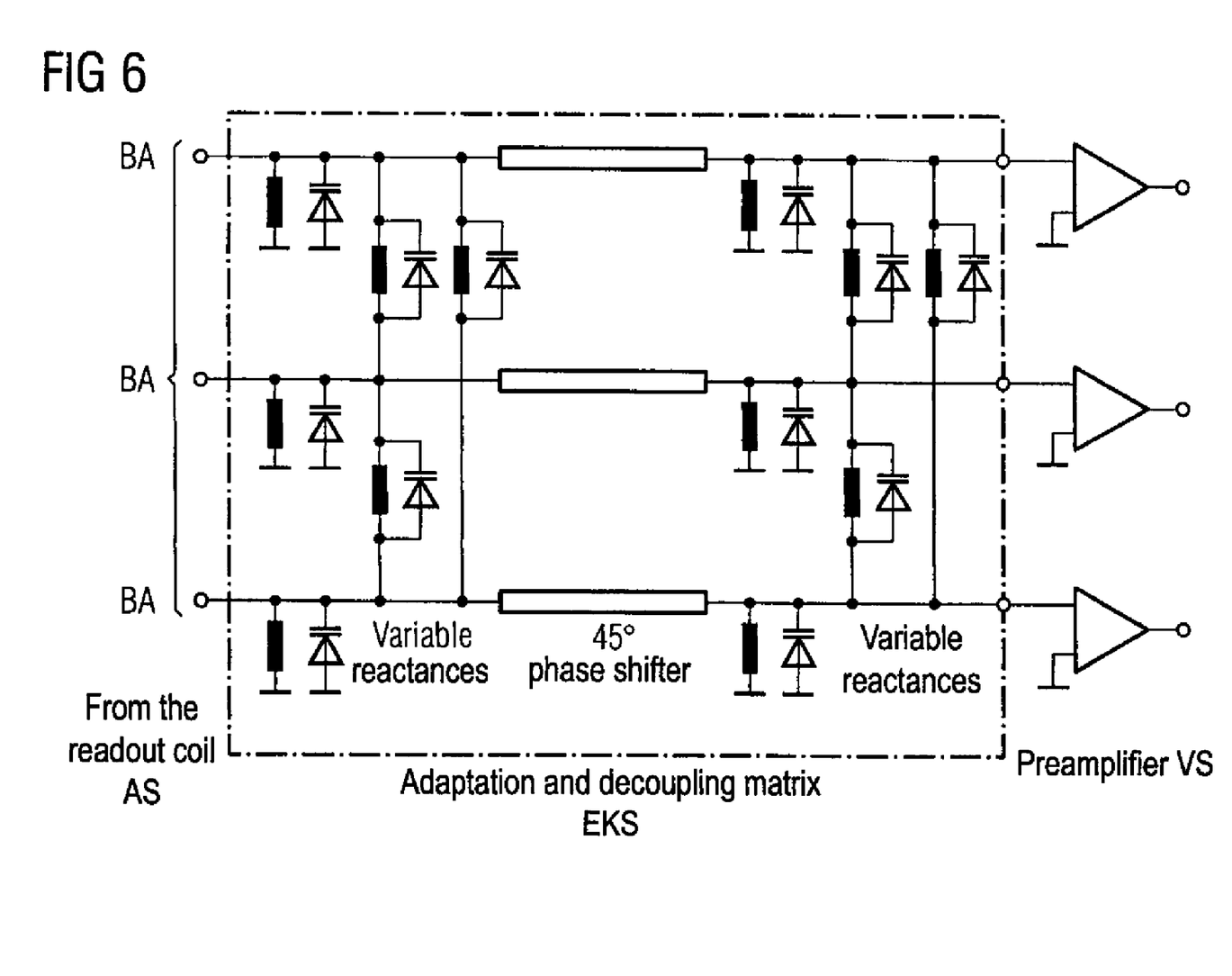
FIG. 6 shows an exemplary decoupling circuit.

FIG. 6 shows an exemplary adaptation and decoupling circuit to minimize a retroaction of utilized preamplifiers.

As illustrated above, a retroaction of the individual antennas of the local coil on the preamplifiers represents an additional problem that leads to an amplified internal noise of the inherently low-noise preamplifiers.

A first solution of this problem is to use an adaptation and decoupling circuit EKS. This is fashioned as an adaptation and decoupling matrix and arranged between the individual antennas BA of the readout coil AS and the preamplifiers VS.

The adaptation and decoupling circuit EKS possesses capacitance diodes and is adjustable via variable reactances for different local coil arrangements.

A second solution (not shown here) to the problem is to reduce the internal noise of the preamplifier via cooling to cryogenic temperatures (for example to 80 K). A significant improvement is thereby achieved in the individual antenna arrays described in the preceding, which are inductively coupled.

Figure 7:
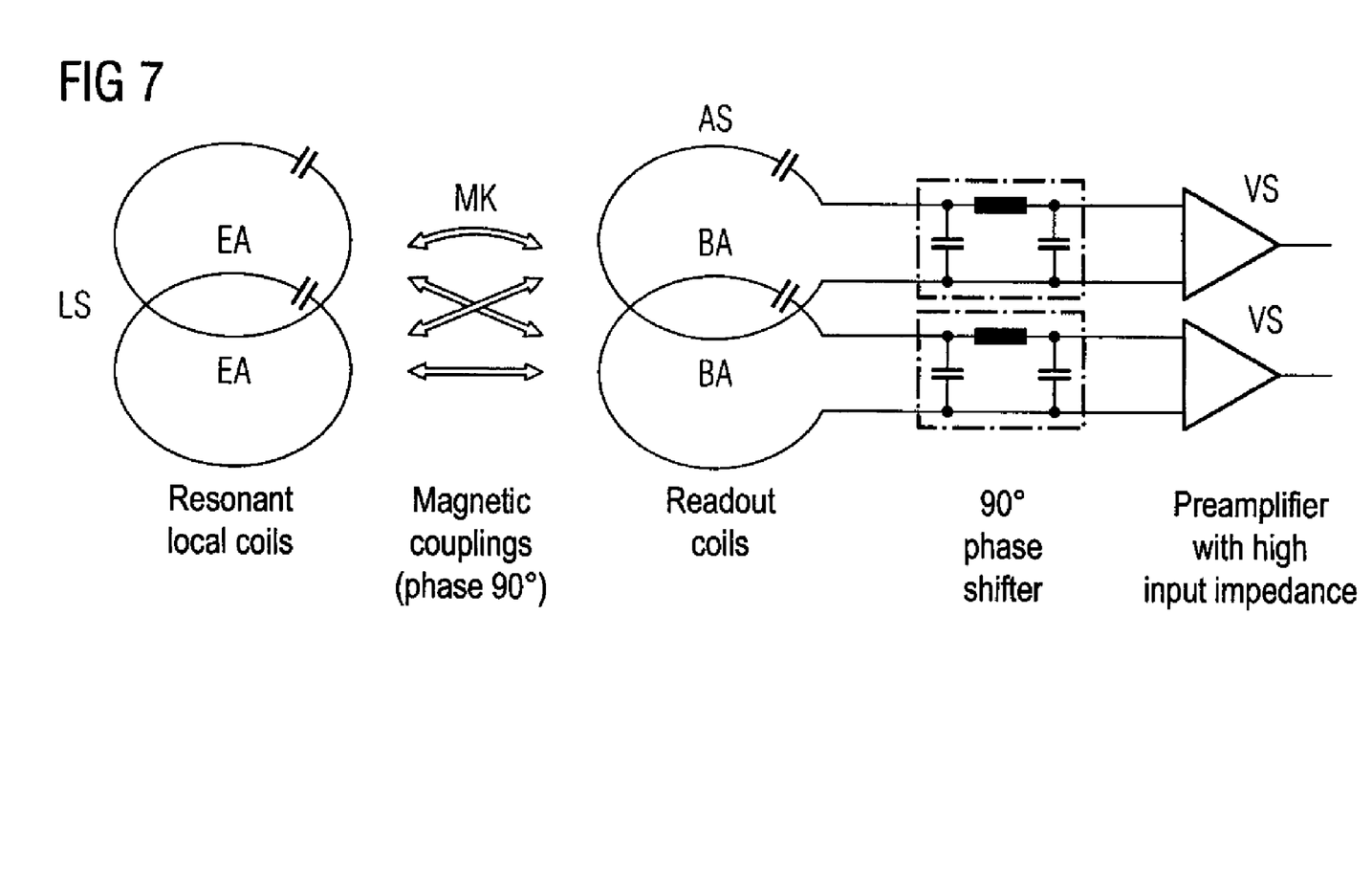
FIG. 7 shows a further version of the inventive arrangement with regard to FIG. 1.

Relative to FIG. 1, FIG. 7 shows an advantageous development of the arrangement according to the invention.

A 90° phase shifter is interconnected between each acquisition antenna BA of the readout coil AS and the respective associated preamplifier VS. Every preamplifier VS thereby exhibits a high input impedance.

Due to the phase (electrical length) of the connection, the input impedance of the preamplifier appears as a high impedance in series with the individual antenna of the coil, such that its resonance is attenuated as strongly as possible. A small effect of patient-dependent load changes and couplings of the individual antennas of the local coil to the acquired signal level is therefore achieved without thereby negatively affecting the signal-to-noise ratio (SNR).

Figure 8:
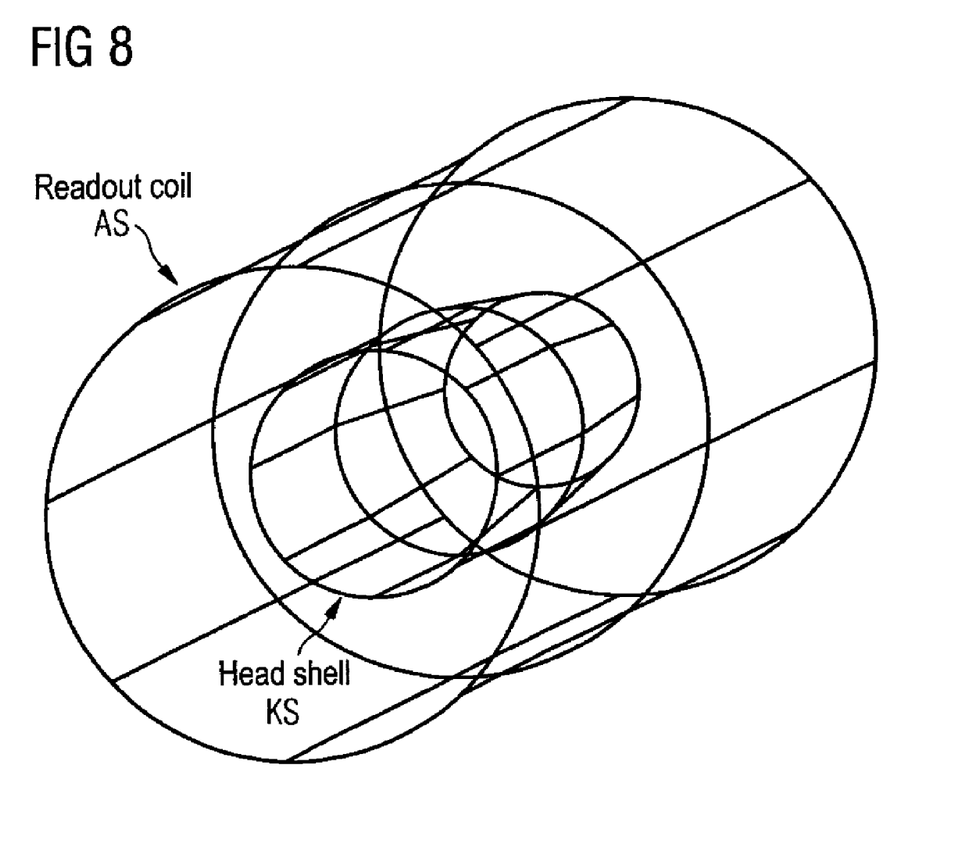
FIG. 8 illustrates a realization of the arrangement according to the invention in a coil helmet.

FIG. 8 shows the arrangement according to the invention for a coil helmet in a principle representation.

Since heads differ from to-be-examined patient to patient, two possibilities for the development of a head coil or, respectively, coil helmet have previously been applied.

A first possibility is to select a coil shape that is large enough for examination purposes for a plurality of possible head shapes and head sizes. However, it is thereby accepted that examination results with a poor SNR will be generated given patients with smaller heads (children, newborns, . . . ) due to an increased distance between head and coil.

A second possibility is to select a number of different coil shapes, of which each individual coil form is suitable for a small percentile of patients to be examined due to the respective dimensions, and examination results with an optimal SNR are ensured from each coil shape.

The coil helmet with inductive coupling (presented here in principle) is suitable for all head shapes and head sizes and possesses a readout coil AS and a local coil.

The readout coil AS is large enough to be able to accommodate all head shapes and head sizes. According to the invention, signals of the local coil can be transferred to the readout coil AS via magnetic coupling with the aid of the readout coil AS.

Furthermore, multiple head shells KS are provided, each of which is individual realized as a flexible hood (comparable to a bathing cap).

Each flexible head shell KS in turn bears a corresponding flexible local coil and is respectively optimized for specific head shapes and head sizes.

A head coil of such a design has the advantage of being able to forego preamplifiers, cables or sheath wave barriers, such that a very flexible local coil can be realized.

Figure 9:
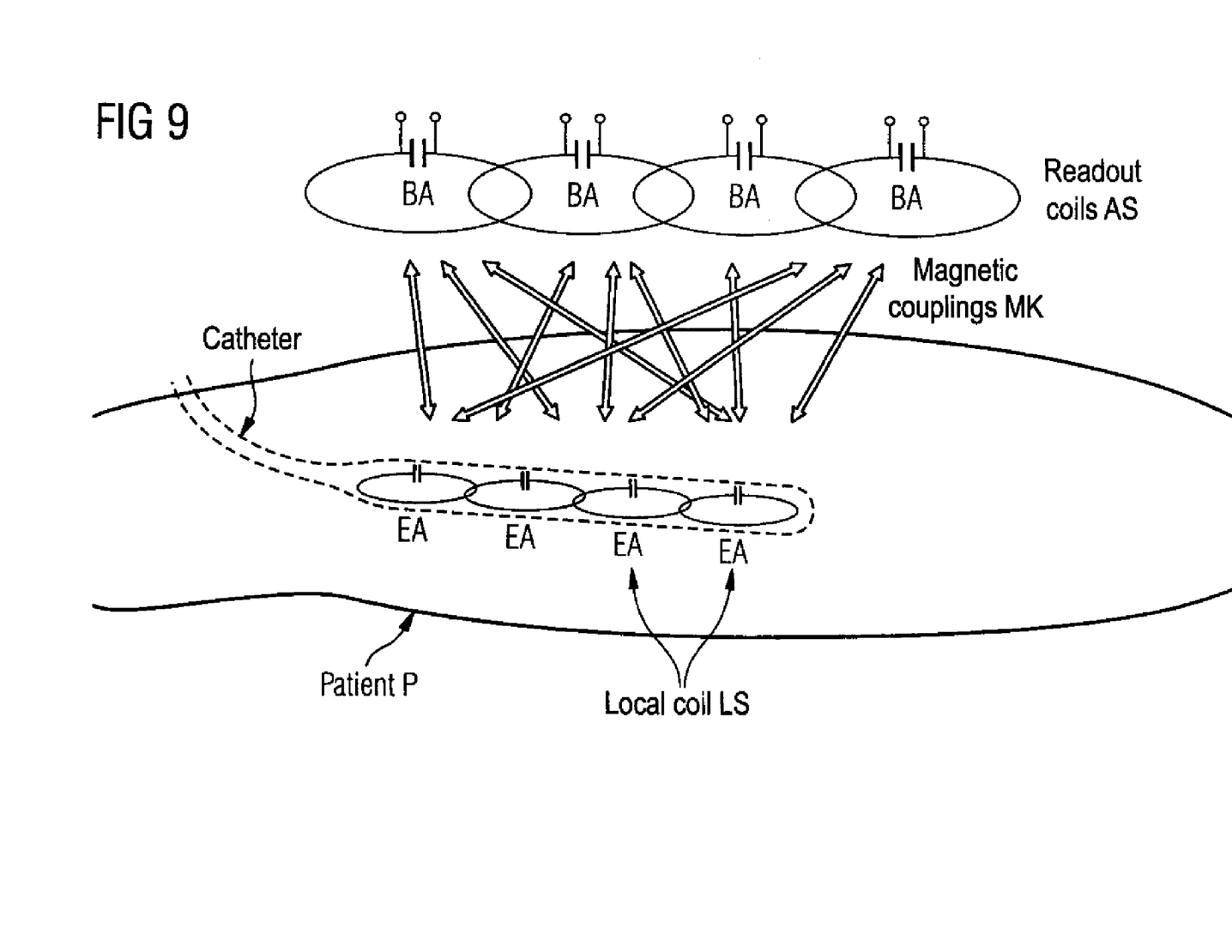
FIG. 9 illustrates a realization of the arrangement according to the invention in a catheter.

FIG. 9 shows a realization of the arrangement according to the invention in a catheter.

An additional possible usage field for inductively coupled coils according to the invention is a local coil LS that is used as an "inside-the-body local coil".

Given conventional intracorporal or, respectively, inside-the-body local coils, the preamplifiers cannot be directly attached to the coil elements due to the necessary small coil dimensions; rather, they must be connected via a longer cable length. Additional noise is caused by the connected cables, and the signal-to-noise ratio (SNR) is worsened.

Moreover, sheath wave barriers are attached to the cables in order to suppress sheath waves arising during the transmission operation. These sheath wave barriers occupy a larger volume that is not available in intracorporal local coils.

Contrarily, via the present invention it is enabled to forego both the preamplifiers and the wired transmission of the MR acquisition signal in the local coil.

It is thereby possible to implement the lifting of the signals of the local coil via readout coil arrays attached posterior or anterior to the patient.

Although modifications and changes may be suggested by those skilled in the art, it is the intention of the inventors to embody within the patent warranted hereon all changes and modifications as reasonably and properly come within the scope of their contribution to the art.

We claim as our invention:

1. An arrangement to transmit magnetic resonance signals comprising:
   a local coil comprised of a plurality of individual antennas that respectively acquire radio-frequency signals in a magnetic resonance data acquisition procedure;

a plurality of amplifiers that respectively amplifies said radio-frequency signals;

a transmission device that transfers the radio-frequency signals from the local coil to the pre-amplifiers; and said transmission device being formed as a readout coil comprising a plurality of individual readout coil antennas, said readout coil antennas being magnetically coupled with the individual antennas of the local coil in a configuration wherein the individual antennas of the local coil and the readout coil individual antennas form a linear MIMO transmission system describable by a transmission matrix.

2. An arrangement as claimed in claim 1 wherein said individual antennas of said local coil are coupled with each other to produce a mode-dependent dispersion with spatially low-frequency modes having an internal resonance that is above an operating frequency of a magnetic resonance system in which the local coil is employed.

3. An arrangement as claimed in claim 2 wherein said local coil is a degenerate birdcage antenna.

4. An arrangement as claimed in claim 3 wherein said degenerate birdcage antenna comprises a plurality of antenna rods respectively having rod capacitances therein, and wherein said mode-dependent dispersion is adjustable by adjusting the respective rod capacitances.

5. An arrangement as claimed in claim 2 wherein said local coil is a loop array with said individual antennas formed respectively by individual coils.

6. An arrangement as claimed in claim 5 wherein said mode-dependent dispersion is set by a geometric overlap of the respective individual coils.

7. An arrangement as claimed in claim 1 wherein said individual antennas of said local coils are disposed in a first plane and wherein said readout coil individual antennas are disposed in a second plane that is parallel to said first plane.

8. An arrangement as claimed in claim 1 wherein said individual antennas of said local coils and said readout coil individual antennas are respectively disposed on cylinder walls that are parallel to each other.

9. An arrangement as claimed in claim 1 wherein said local coil is movable and is configured for placement substantially adjacent to a patient, and wherein said readout coil is configured as a stationary part of a magnetic resonance apparatus with which said local coil is employed.

10. An arrangement as claimed in claim 1 comprising a cryogenic cooling arrangement that cools the readout coil individual antennas.

11. An arrangement as claimed in claim 1 comprising a transmission coil comprised of a plurality of transmission coil individual antennas between said local coil and said readout coil, said individual antennas of said local coil and said transmission coil individual antennas being connected via a first magnetic coupling, and the transmission coil individual antennas and the readout coil individual antennas being connected via a second magnetic coupling.

12. An arrangement as claimed in claim 1 wherein said readout coil individual antennas are respectively connected to said preamplifier.

13. An arrangement as claimed in claim 12 comprising an adaptation and decoupling circuit connected between each readout coil individual antenna and the preamplifier connected thereto.

14. An arrangement as claimed in claim 12 comprising a cryogenic cooling arrangement that cools the preamplifiers.

15. An arrangement as claimed in claim 12 comprising a phase shifter connected between each readout coil individual antenna and the preamplifier connected thereto.

16. An arrangement as claimed in claim 1 comprising a head shell configured for a head examination of a patient, said head shell containing said individual antennas of said local coil, and wherein said readout coil is configured to accommodate a plurality of different head shapes and head sizes, and wherein said readout coil individual antennas are connected with the individual antennas of the local coil via magnetic coupling.

17. An arrangement as claimed in claim 16 wherein said head shell is a flexible hood that conforms to the head of a patient to be examined.

18. An arrangement as claimed in claim 1 wherein said local coil is configured for intracorporeal application and wherein said readout coil is configured for extracorporeal application.

19. An arrangement as claimed in claim 1 wherein said local coil is a flexible cover configured for placement over the body of a patient.

20. An arrangement as claimed in claim 1 wherein said local coil is configured to also radiate radio-frequency signals into a patient to excite nuclear spins to generate magnetic resonance signals that are detected by the local coil and supplied therefrom to the readout coil.

* * * * *